United States Patent
Kim et al.

(10) Patent No.: US 10,324,072 B2
(45) Date of Patent: Jun. 18, 2019

(54) POLYDIACETYLENE WATER SENSORS

(71) Applicant: THE REGENTS OF THE UNIVERSITY OF MICHIGAN, Ann Arbor, MI (US)

(72) Inventors: Jinsang Kim, Ann Arbor, MI (US); Sungbaek Seo, Ann Arbor, MI (US); Youngchang Yu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 268 days.

(21) Appl. No.: 15/114,907

(22) PCT Filed: Feb. 20, 2015

(86) PCT No.: PCT/US2015/016878
§ 371 (c)(1),
(2) Date: Jul. 28, 2016

(87) PCT Pub. No.: WO2015/127249
PCT Pub. Date: Aug. 27, 2015

(65) Prior Publication Data
US 2016/0349223 A1    Dec. 1, 2016

Related U.S. Application Data

(60) Provisional application No. 61/942,826, filed on Feb. 21, 2014.

(51) Int. Cl.
*G01N 21/75* (2006.01)
*G01N 31/22* (2006.01)
(Continued)

(52) U.S. Cl.
CPC ............. *G01N 31/222* (2013.01); *B05D 1/18* (2013.01); *B05D 3/007* (2013.01); *B82Y 30/00* (2013.01); *B82Y 40/00* (2013.01)

(58) Field of Classification Search
CPC ........ G01N 31/222; B05D 3/007; B05D 1/18; B82Y 30/00; B82Y 40/00
See application file for complete search history.

(56) References Cited

U.S. PATENT DOCUMENTS 6,063,486 A    5/2000  Kobayashi
6,440,056 B1   8/2002  Singh et al.
(Continued)

FOREIGN PATENT DOCUMENTS

WO    WO-2008048241 A2    4/2008

OTHER PUBLICATIONS

Agh-Atabay et al.,"Synthesis and Characterisation of Carboxylic Acid and Diphenylphosphine Derivatives in the I ,3-Diyne Series: Spectral Properties of Polydiacetylene Carboxylates" Polymer International 31 (1993) 367-374 (Year: 1993).*
(Continued)

*Primary Examiner* — Dennis White
(74) *Attorney, Agent, or Firm* — Harness, Dickey & Pierce, P.L.C.

(57) ABSTRACT

Moisture sensing color change compositions are built of nanofibers of suitable small dimension based on diacetylene monomers that are polymerized in situ in a dried film containing a hygroscopic polymer that is bound to the nanofibers either directly or through crosslinkers.

7 Claims, 2 Drawing Sheets

(51) Int. Cl.
  *B05D 1/18* (2006.01)
  *B05D 3/00* (2006.01)
  *B82Y 40/00* (2011.01)
  *B82Y 30/00* (2011.01)

(56) References Cited

U.S. PATENT DOCUMENTS

| | | |
|---|---|---|
| 6,589,731 B1 | 7/2003 | Chen et al. |
| 6,979,543 B2 | 12/2005 | Chen et al. |
| 6,984,528 B2 | 1/2006 | Reppy et al. |
| 8,225,641 B2 | 7/2012 | Wang et al. |
| 8,633,140 B2 | 1/2014 | Kim et al. |
| 9,523,683 B2 | 12/2016 | Kim et al. |
| 2007/0275371 A1 | 11/2007 | Sim et al. |
| 2009/0291454 A1 | 11/2009 | Sim et al. |
| 2011/0102795 A1 | 5/2011 | Peng et al. |

OTHER PUBLICATIONS

Kim et al, "Polydiacetylene Supramolecules Embedded in PVA Film for Strip-type Chemosensors" Chemistry Letters vol. 35, No. 6 (2006) pp. 560-561 (Year: 2006).*

International Search Report and Written Opinion for PCT/US2015/016878, dated Jun. 30, 2015; ISA/KR.

Kim, Hyong-Jun, et al., "Highly Emissive Organic Nanoparticles for Targeted Immunofluorescence Labeling." Polymeric Materials: Science & Engineering Preprints, American Chemical Society, vol. 98, pp. 394-395 (2008).

Kim, Hyong-Jun, et al., "Highly Emissive Self-Assembled Organic Nanoparticles having Dual Color Capacity for Targeted Immunofluorescence Labeling." Advanced Materials, vol. 20, pp. 1117-1121 (2008).

Lee, Jiseok et al., "Fluorogenic Conjugated Polymer Fibers from Amphiphilic Diacetylene Supramolecules." Macromolecular Research, vol. 16, No. 1, pp. 73-75 (2008).

Lee, Jiseok et al., "Polydiacetylene Liposome Arrays for Selective Potassium Detection." Journal of the American Chemical Society, vol. 130, pp. 5010-5011 (2008).

Lee, Jiseok et al., "Polydiacetylene-Liposome Microarrays for Selective and Sensitive Mercury(II) Detection." Advanced Materials, vol. 21, pp. 3674-3677 (2009).

Lee, Joosub et al., "Hydrochromic conjugated polymers for human sweat pore mapping." Nature Communications, vol. 5, No. 3736, doi: 10.1038/ncomms4736 (2014).

* cited by examiner

POLYDIACETYLENE WATER SENSORS

CROSS REFERENCE TO RELATED APPLICATIONS

This application is a U.S. National Phase Application under 35 U.S.C. 371 of International Application No. PCT/US2015/016878 filed on Feb. 20, 2015 and published as WO 2015/127249 A1 on Aug. 27, 2015. This application claims priority to U.S. Provisional Application No. 61/942,826 filed on Feb. 21, 2014. The entire disclosures of all of the above applications are incorporated herein by reference.

GOVERNMENT SUPPORT

This invention was made with U.S. government support under DMR0644864 awarded by the National Science Foundation. The Government has certain rights in the invention.

INTRODUCTION

Detection of water, either as vapor or liquid, in industrial or health care environments is crucial for proper operations of systems, or to monitor the health and safety of the environment. In the medical field, the presence of water in tissue can signal the need for further treatment, such as by further drying to prepare a site for surgery. In various environments, the presence of water indicates for example the breakdown of controlled devices such as seals.

In all these cases, a convenient method of visually determining the presence of water in an environment would be desirable. In Kim et al., U.S. publication number US2011/0059867 published Mar. 10, 2011, self-assembled liposomes containing polydiacetylenes were developed that change color upon covalent bonding of target molecules like melamine or nerve gas agents. Unfortunately, the liposomes containing the polydiacetylenes, being classified as so-called zero dimensional, were not sensitive to the presence of moisture. Lee et al., in Nature Communications 5:3736 DOI:10.1038/ncomms4736 published at www.nature.com/naturecommunications, discloses hydrochromic materials based on supramolecularly assembled polydiacetylenes that are sensitive to moisture in the form of water vapor in high humidity environments. There is a continuing need for simple and reliable means for detecting water, especially indicating the presence of water by a color change.

SUMMARY

It is now been found that certain nanofibers of suitable small dimension can be made into compositions that change color upon exposure to water or water vapor. The nanofibers are based on diacetylene monomers, with the moisture sensing film further containing a hygroscopic polymer that is bound to the nanofibers either directly or through crosslinkers. To manufacture the moisture sensors, a suspension of the nanofibers is combined with a hygroscopic polymer with an optional crosslinker to bind the two. Then, diacetylene moieties of the nanofibers are polymerized in situ with the hygroscopic polymer, and the resulting composition is applied as a film on a substrate and dried. The result is a material that changes color upon exposure to the moisture for water.

It is believed that the sensor operates by a mechanism of mechanochromism. Briefly, in the dried state, the conjugated double and triple bond system of the polydiacetylene nanofiber has an electronic state giving it a blue color. Upon exposure of the film to water, the hygroscopic polymer in the sensor swells. This swelling is believed to act mechanically on the nanofibers and the network of double and triple bonds existing throughout the film. This perturbation of the pi structure of the nanofibers resulting from the swelling of the polymer is believed to change the electronic configuration to such an extent that a visible color change is observed.

To make nanofibers with a suitably small dimension, lithium ions are combined with certain diacetylene monomers and combined with a hygroscopic anionic or cationic polymer. If the monomer making up the nanofibers and the hygroscopic polymer are of the same charge, a multivalent crosslinker (exemplified by divalent or trivalent cations) can be used. The resulting composition is then applied to a substrate, dried, and exposed to a radiation to polymerize the diacetylene moieties of the monomers. The result is a film that changes color upon exposure to vapor, and which can be provided in various physical forms as probes and the like.

In another embodiment not relying on the nanofibers, a water sensor is made by combining a salt of a diacetylene carboxylic acid and a water-soluble polyvinyl alcohol or other polymer on a substrate and photopolymerizing conjugated triple bonds in the diacetylene carboxylic acid in situ. The resulting composition adopts a blue color, and changes to red when exposed to moisture in the form of liquid water. In various embodiments, the sensor does not respond to the presence of relative humidity but only to the presence of liquid water. This makes the sensor suitable for use in a humid environment (such as the oral cavity) where the purpose is to detect liquid water in a tissue.

DRAWINGS

DESCRIPTION

Figure 1:
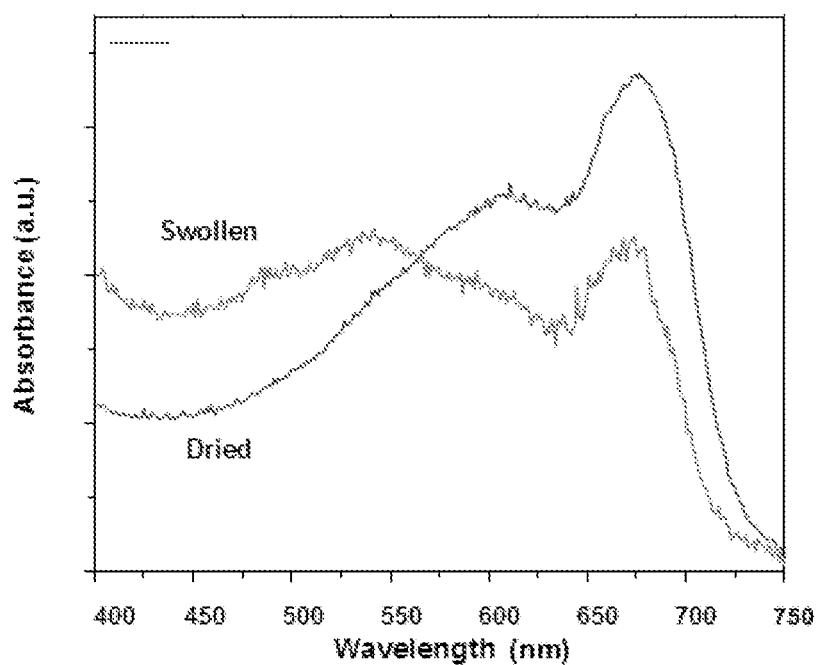
FIG. 1 is an absorbance spectrum of a dry and a wet film, showing colorimetric transition.

In one aspect, water sensors are made from nanofibers that are formed from lithium salts of certain diacetylene monomers. Triple bonds (acetylene groups) in the monomer are polymerized in the presence of certain hygroscopic polymers on a substrate to form a film that changes color from blue to red in the presence of moisture. This is called the nanofiber aspect in the description below.

In another aspect, the sensors contain potassium, rubidium, or cesium salts of diacetylene carboxylic acids that are applied to a substrate. The coated salts are then themselves coated with a water soluble polymer, and triple bonds (acetylene groups) in the diacetylene carboxylic acids are photopolymerized in situ to make the sensors.

1. The Nanofiber Aspect

In the nanofiber aspect, the present technology provides a moisture sensor containing a substrate and a moisture sensitive film applied on the substrate. When the film is exposed to water in the form of liquid or water vapor, the color of the film is observed to change. The dry film contains a hygroscopic polymer that swells when contacted with water. In the dry film, the hygroscopic polymer is intimately mixed with a polydiacetylene network prepared by exposing a nanofiber containing the diacetylene group to ultraviolet (UV) radiation. The nature of the polydiacetylene is that the film appears to be blue when dry. When film is exposed to moisture, the hygroscopic polymer absorbs some of the water and swells. Swelling of the hygroscopic polymer in turn disturbs or perturbs the three dimensional polydiacetylene network in which the polymer is embedded. By a mechanism called mechanochromism, the swelling of the hygroscopic polymer in the sensor film perturbs the electronic structure of the polydiacetylene, with the result that the color is observed to visually change, in most cases to a red color.

In one embodiment, a method of making such a moisture sensor is provided. The sensor contains a substrate and an applied moisture sensitive film. The method involves:
a) combining a diacetylene monomer with lithium ion in a solution to make a nanofiber suspension;
b) combining the nanofiber suspension with a composition comprising a hygroscopic polymer to make a nanofiber/polymer suspension;
c) coating the combined suspension of the nanofiber and the hygroscopic polymer of step b) on a substrate;
d) optionally exposing the composite polymer coated substrate to a crosslinker solution;
e) drying the coating of step d) on the substrate;
f) exposing the dried product of step e) to ultraviolet radiation In another embodiment, a method of making such a moisture sensor involves:
a) combining a diacetylene monomer with lithium ion in a solution to make a nanofiber suspension;
b) combining the nanofiber suspension with a composition comprising a hygroscopic polymer to make a nanofiber/polymer suspension;
c) optionally adding a crosslinker to the nanofiber/polymer suspension;
d) coating the crosslinked polymer of step c) on a substrate;
e) drying the coating of step d) on the substrate;
f) exposing the dried product of step e) to ultraviolet radiation In this way a crosslinker is added before or after coating the substrate, depending on the nature of the crosslinker.

In the methods described herein, the monomer is a chemical compound or composition containing a tail section connected to a head section. The tail section of the monomer contains a carbon chain of 10 or more carbon atoms, while the head section contains a hydrophilic organic moiety that promotes formation of nanofiber in the presence of lithium ion. The carbon chain of the tail also includes two adjacent conjugated triple bonds, and the head of the monomer carries an organic functional group that interacts either 1) with the crosslinker when the nanofiber and the hygroscopic polymer are of like charge, or 2) directly with an oppositely charged hygroscopic polymer to connect the nanofiber to the hygroscopic polymer. Further details of the monomer, the nanofiber suspension, the hygroscopic polymer, the crosslinker, the substrate, and the steps of drying and exposing to UV radiation are described further herein.

In another embodiment, a method of making a moisture sensor that indicates the presence of water by changing colors from blue to red comprises:
a) combining a suspension of nanofibers with a solution of a polymer that swells upon contact with water;
b) coating the product of the step a) onto a substrate
c) dipping the product of the step b) into a crosslinker solution, or exposing the product of step b) to a solution of the crosslinker, wherein the crosslinker interacts with functional groups on the nanofibers and with functional groups on the polymer;
d) drying the coating on the substrate; and
e) exposing the dried coating to ultraviolet radiation.

In another embodiment, a method of making a moisture sensor that indicates the presence of water by changing colors from blue to red comprises:
a) combining a suspension of nanofibers with a solution of a polymer that swells upon contact with water;
b) adding a crosslinker to the combination of step a), wherein the crosslinker interacts with functional groups on the nanofibers and with functional groups on the polymer;
c) coating the crosslinked product of the step b) onto a substrate;
d) drying the coating on the substrate; and
e) exposing the dried coating to ultraviolet radiation.

In this way, the crosslinker is applied before or after the coating step.

In this method, the nanofibers are made from a plurality of monomers containing conjugated triple bonds and are characterized by a diameter of less than 50 nanometers.

In another aspect, methods of making a moisture sensor involve combining a nanofiber of having a diameter less than 50 nanometers and hygroscopic polymer that swells upon contact with water to make a moisture sensor that apparently operates by a mechanism of mechanochromism. In one aspect, a method of making a suspension of suitable nanofibers is provided. The nanofibers have a diameter less than 50 nanometers and the method for making them involves combining a monomer composition and a source of lithium ions in solution. The monomer composition contains a diacetylene monomer having structure Formula (I)

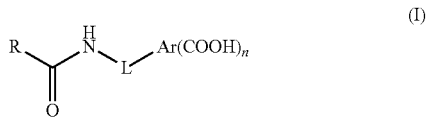

In Formula (I), R is a hydrocarbyl group of 10 or more carbon atoms and contains at least 2 conjugated triple bonds. Further in Formula (I), L is a direct bond or a divalent aliphatic linking group having 6 non-hydrogen atoms or less. Further, Ar is an aryl ring or aryl ring system, and n is 1 to 5. It has been observed that when monomers of Formula (I) are combined in solution with a source of lithium ions, suitable nanofiber suspensions can be prepared that can be further used to make the moisture sensors of the invention.

Thus, it can be seen that the technology includes a moisture sensitive composition that changes color from blue to red when contacted with water or water vapor. The moisture sensitive composition comprises a dry film containing polydiacetylene nanofibers of diameter less than 50 nanometers and further contains a hygroscopic polymer that swells upon contact with water or water vapor.

In addition to the working examples given further below, the following description of various aspects of the technology is intended to apply to various embodiments and aspects of the invention laid out above and in the claims. Unless context provides otherwise, it is intended that various features of the monomer, nanofibers, hygroscopic polymer, crosslinker, and substrate can be mixed and matched to provide other embodiments of the invention.

Diacetylene Monomers

As noted, the diacetylene monomers have a tail section and head section. The tail section contains a carbon chain of 10 or more carbon atoms and also contains conjugated triple bonds. Conjugated means that two carbon triple bonds are disposed in 1,3-configuration, and are disposed such that they can polymerize in 1,4-fashion with other conjugated triple bonds on other monomers within the same fiber. The conjugated triple bond system contains at least two triple bonds, as shown in the examples.

The head of the monomer contains a hydrophilic organic moiety that promotes formation of nanofiber in the presence of lithium ion and also carries an organic functional group that interacts 1) with the crosslinker when the nanofiber monomer and the hygroscopic polymer are of like charge, or 2) directly with an oppositely charged hygroscopic polymer. Interaction of the organic functional group with hygroscopic polymer either directly without a crosslinker or indirectly through a crosslinker plays an important role in forming the moisture sensor film.

In various embodiments, the tail comprises a hydrocarbyl group containing 18-30 carbon atoms or, in another embodiment, containing 20-28 carbon atoms. These numbers of carbon atoms include those that are involved in the conjugated triple bond system of the tail.

The head section in various embodiments contains an aromatic group, which is believed to contribute to the formation of nanofibers through pi-stacking interactions. In preferred embodiments, the head section further contains one or more carboxyl groups. These carboxyl groups upon interaction with a lithium ion provide negatively charged groups on the fiber for interaction with the crosslinker or directly with an oppositely charged hygroscopic polymer. In various embodiments, the head section contains an amide group —C(O)NH—.

In various embodiments, the monomer containing the head section and tail section is represented by Formula (I) above.

In Formula (I), R is a hydrocarbyl group of the tail that contains 10 or more carbon atoms and contains conjugated triple bonds. L represents a direct bond or a divalent aliphatic linking group having 6 non-hydrogen atoms or less. Ar represents an aryl ring or aryl ring system, and n is a number 1 to 5 indicating how many carboxyl groups are attached to the aryl ring or the aryl ring system. In one embodiment, L is direct bond and n is 2 or 3. An example of Ar is a phenyl ring. In various embodiments, the hydrocarbyl group R has 10-40 carbon atoms, for example, 18-30 carbon atoms. Formula (I) also shows the presence of the amide group that is formally assigned to the "head" of the monomer.

The linking group L is either a direct bond or an aliphatic group containing 6 non-hydrogen atoms or less. Examples include alkylene, oxyalkylene, and alkoxyalkylene groups. In various embodiments, the linking group L is a linear connecting group containing 1 to 6 non-hydrogen atoms, including carbon, nitrogen, and/or oxygen.

In a particular embodiment, the monomer is represented by Formula (II):

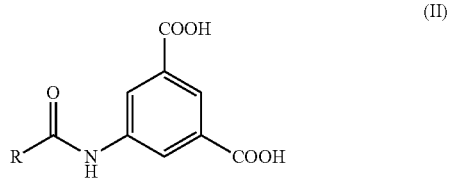

(II)

where R is a hydrocarbyl group as defined above. Formula (II) shows a monomer of Formula (I) wherein L is a direct bond, Ar is a phenyl group, and n is 2.

Nanofibers

Upon interaction with lithium ions, diacetylene monomers described herein form a suitable nanofibers for the water sensors. It is observed that, by using lithium ions, nanofibers are formed having a diameter less than 50 nanometers. In various embodiments, the nanofibers are characterized by a diameter of 40 nanometers or less, 30 nanometers or less, or about 20 nanometers. In a first step of making suitable moisture sensors, a diacetylene monomer is combined in a solution with lithium ion to make a nanofiber suspension. The amount of lithium ion used is less than the stoichiometric needed to neutralize all of the carboxyl groups, leaving organic moieties on the monomer free to interact with the crosslinker and/or hygroscopic polymer, as further provided herein. In various embodiments, nanofibers are provided having a diameter less than 50 nanometers, or about 20 nanometers. In contrast to the interaction with lithium, it has been observed that treatment of the polydiacetylene monomer with sodium ions provides unsuitable nanofibers having a diameter of about 50 nanometers or greater. While treating the polydiacetylene monomers with potassium ion leads to formation of nanofibers, the nanofibers have a diameter of about 50 nanometers and are not suitable for use in the water sensors described herein.

Hygroscopic Polymers

Hygroscopic polymers are those that swell when in contact with water, including moisture vapor. Although the invention is not limited to theory, it is believed that swelling of the hygroscopic polymer in the dried film contributes to a perturbation of the polydiacetylene network with which hygroscopic polymer in the film is intimately connected. This perturbation in suitable circumstances can lead to an observed color change, as demonstrated further in the working examples. Examples of polymers that absorb moisture from the air and tend to swell upon contact with water include nylon, acrylonitrile butadiene styrene (ABS), polycarbonate, cellulose, poly(methyl methacrylate), sodium polyacrylate, polyacrylamide, and crosslinked polyethylene oxide. Another useful swellable hygroscopic polymer is alginate, used in the examples as the sodium salt. Hygroscopic polycations include poly(ethyleneimine), poly (allylamine), and chitosan, in non-limiting fashion.

There are two different ways of determining whether a material is swellable or hygroscopic. One is based on weight gain before and after exposure to moisture. The other is based on volume change. If the material gains weight upon exposure to water, it is considered to be swellable and hygroscopic. A general way to measure swelling ratio is to determine a weighing (or volumetric) ratio between values after/before immersing into water for a certain duration. In cases of non-swellable materials, the ratio has a value of 1, indicating no weight gain or volumetric change upon exposure to water. In one embodiment, hygroscopic polymers are those having a swelling ratio of greater than 1.

A suitable hygroscopic polymer is one that swells upon exposure to water. Swelling upon exposure to water can be measured by a so-called swelling ratio. To determine the selling ratio, dried hydrogels are weighed as dried state ($W_d$). The dried hydrogels were immersed in 1 ml of deionized water for 1 hour. The hydrogels were removed and were blotted with a paper towel to remove excess water on surface. Then, swollen hydrogels were weighed as swollen state ($W_s$). The swelling ratio ($Q_s$) of test samples was calculated from the equation $Q_s=(W_s-W_d)/W_d$.

In various embodiments, a polymer is considered swellable and thus suitable for use in the water sensors if the swelling ratio has a value of greater than 1, of 2 or greater, of 3 or greater, or of 4 or greater. The swelling ratio is a function of the nature of the polymer and the amount of crosslinking that it undergoes when combined with nanofibers in suspension. In any particular system, the amount of polymer and crosslinker can be varied to find a suitable combination having a desirable swelling ratio. In various embodiments, a swelling ratio of 30-35 is practical to achieve and has given good results.

Crosslinker

If the diacetylene monomer (in particular the head section of the monomer) and the hygroscopic polymer have functional group with opposite charges, those opposite charges can interact with one another to form the direct interaction needed to make a suitable water sensor, once the composition containing the monomer and the hygroscopic polymer are dried to a film on a substrate. In preferred embodiments, the head of the monomer contains negatively charged groups arising from carboxyl groups. In this situation, an oppositely charged hygroscopic polymer containing polycations (such as poly(ethyleneimine), poly (allylamine), and chitosan) can form suitable intermolecular interactions even without an added crosslinker.

On the other hand, when the functional groups of monomer and of the hygroscopic polymer are of similar or like charge, a crosslinker is generally used to provide the intermolecular interaction necessary for proper operation of the moisture sensor. In a non-limiting example, when the monomer and polymer are both negatively charged it is possible to add a divalent or trivalent cation as a crosslinker. Non-limiting examples include $Ca^{2+}$, $Be^{2+}$, $Mg^{2+}$, $Sr^{2+}$, $Al^{3+}$, and $Fe^{3+}$ ions. The cations are conveniently added, for example, as the chlorides. Thus, in an embodiment described in the examples, the crosslinker is a solution of calcium chloride ($CaCl_2$).

For each combination of monomer, hygroscopic polymer, and crosslinker, an optimum concentration of polymer and crosslinker can be found empirically as a combination that gives a suitable swelling ratio, such as a ratio on the order of 30-35. The amount of crosslinker used is sufficient to keep the hygroscopic polymer from simply dissolving in the solvent. This concept is illustrated in the working examples where calcium ions are used as the crosslinking agent between the nanofiber and the alginate (hygroscopic polymer).

Substrate

After the diacetylene monomer and lithium ion are combined in the solution to make a nanofiber suspension, then after the nanofiber suspension is combined with a composition containing a hygroscopic polymer to make a nanofiber/polymer suspension, and after a crosslinker is optionally added to the suspension, the process provides for crosslink product onto a substrate. The nature of the substrate is not particularly limited, but it is adapted to the environment and application to which the sensor will be put. For example, if it is intended to detect moisture in an atmosphere, such as would be useful for detecting leaks or monitoring the effectiveness of molecular or other drying materials, the suspension can be coated on to a cheap film-like substrate suitable for pinning to a clamp or installing on a bracket within a system to be monitored. In other applications, the film can be placed on substrates suitable for use to probe tissues or the like where the presence of moisture or not indicates suitability for further treatment. For example, the suspension can be coated as a film onto a more or less rigid tip disposed on a probe suitable for checking moisture in gums or other oral tissue.

Conventional technologies can be used to coat the suspension onto the substrate. These include spin coating, dip coating, contact coating (for example, using a doctor blade), spraying, and casting.

After application, the coated suspension is dried to provide a film on the substrate. Drying is accomplished in conventional drying ovens, in a non-limiting example.

Polymerization of the Diacetylene Monomer

After drying, the film is exposed to radiation such as ultraviolet radiation, which promotes the polymerization of the conjugated diacetylene group of the monomer. It is believed that such polymerization involves forming a three dimensional network of alternating triple and double bonds among the monomers in the nanofiber. At the same time, the three dimensional network tightly interacts with the hygroscopic polymer that interacts ionically with the monomer either directly or through operation of the crosslinker. The degree of crosslinking needed for obtaining suitable sensors, can be determined empirically guided by experience and the working examples provided herein.

2. Carboxylic Salt Aspect

In this aspect, the potassium, cesium, or rubidium salt of a diacytelene carboxylic acid is coated onto a substrate along with a water soluble polymer. The coated composition is then crosslinked in situ by photopolymerization with ultraviolet light to make a sensor that indicates the presence of water by exhibiting a color change.

In one embodiment, a method of making a sensor is provided. The sensor changes color upon exposure to moisture. The method involves coating a solution of a carboxylate salt on a substrate, drying the coated substrate, exposing the dried substrate to a solution of a water-soluble polymer and irradiating the coated substrate with ultraviolet radiation. The carboxylate salt is a potassium, cesium, or rubidium salt of a carboxylic acid that contains a carboxylate head and an aliphatic tail. The aliphatic tail contains two conjugated triple bonds.

In various embodiments, the salt is a potassium salt, a rubidium salt, or a cesium salt. The carboxylic acid is selected from those containing 16 to 30 carbon atoms, for example from 18-28 carbon atoms. In various embodiments, the substrate is selected from paper, paperboard, and other materials. In various embodiments, a paper substrate is cut and rolled into a paper-tip to form a sensor.

In another embodiment, a method of detecting the presence of moisture in an environment involves contacting the environment with a sensor made according to the methods described herein. The sensor changes color in presence of the moisture. In specific embodiments, the sensor changes from blue to red when it is exposed to moisture in the environment.

In various embodiments, the environment in which moisture is to be sensed includes biological tissue, such as the tissue found in an oral cavity. In certain embodiments, the environment in which moisture is to be determined includes a gas. However, in other applications, such as the use of the sensors to detect water in tissue such as gums, it is an advantage if the sensor does not change color when exposed to a relative humidity in a gas, but only responds to presence of liquid moisture in the tissue.

In another embodiment of the invention, a water sensor that changes color from blue in the dry state to red in the presence of water is provided. The sensor comprises a composition adhered to a substrate, wherein the composition contains a potassium, rubidium, or cesium salt of a polydiacetylene carboxylic acid and a water-soluble polymer.

A water sensor that changes color from blue in the dry state to red in the presence of water is also described as comprising a substrate, a polymerized diacetylene carboxylate salt coated on the substrate, and a water soluble polymer disposed on the substrate over the polymerized diacetylene carboxylate salt, wherein the carboxylate salt is a potassium, rubidium, or cesium salt of a carboxylic acid comprising a carboxylate head and an aliphatic tail, wherein the aliphatic tale comprises two conjugated triple bonds. The water-soluble polymer comprises polyvinyl alcohol in a non-limiting embodiment. For convenience, the sensor is described as having a polymerized diacetylene carboxylate salt coated on the substrate to describe the structure resulting when the coated carboxylate salt, which contains conjugated triple bonds, is exposed to ultraviolet radiation after a water soluble polymer is coated on the substrate to cover the carboxylate salt.

Further aspects of these embodiments will now be described. It is understood that various specific examples of the components described herein can be combined to provide embodiments of the invention.

meant that the carbon chain of the carboxylic acid includes conjugated triple bonds. It may also contain other structures or functional groups that do not interfere with its operation in the sensor described herein. In the diynoic acids, at least two triple bonds are conjugated with one another. The conjugated triple bonds occur at various locations along the hydrocarbon chain. Non-limiting examples include those found at the 5,7-position, the 6,8-positions, and 10,12-positions in the carboxylic acid.

The carboxylate salts are made in a conventional way by combining a carboxylic acid with a base in solution. In a non-limiting example, the carboxylate salt is made by adding an aqueous solution of a base such as KOH into a solution of the carboxylic acid in a suitable solvent such as tetrahydrofuran (THF).

Suitable carboxylate salts are selected to achieve proper sensing operation in a given environment. Non-limiting examples include 10,12-pentacosadiynoic acid (PCDA), 10,12-tricosadiynoic acid (TCDA), and 8,10-heneicosadiynoic acid (HCDA). For reference, these structures are drawn in Formula (III).

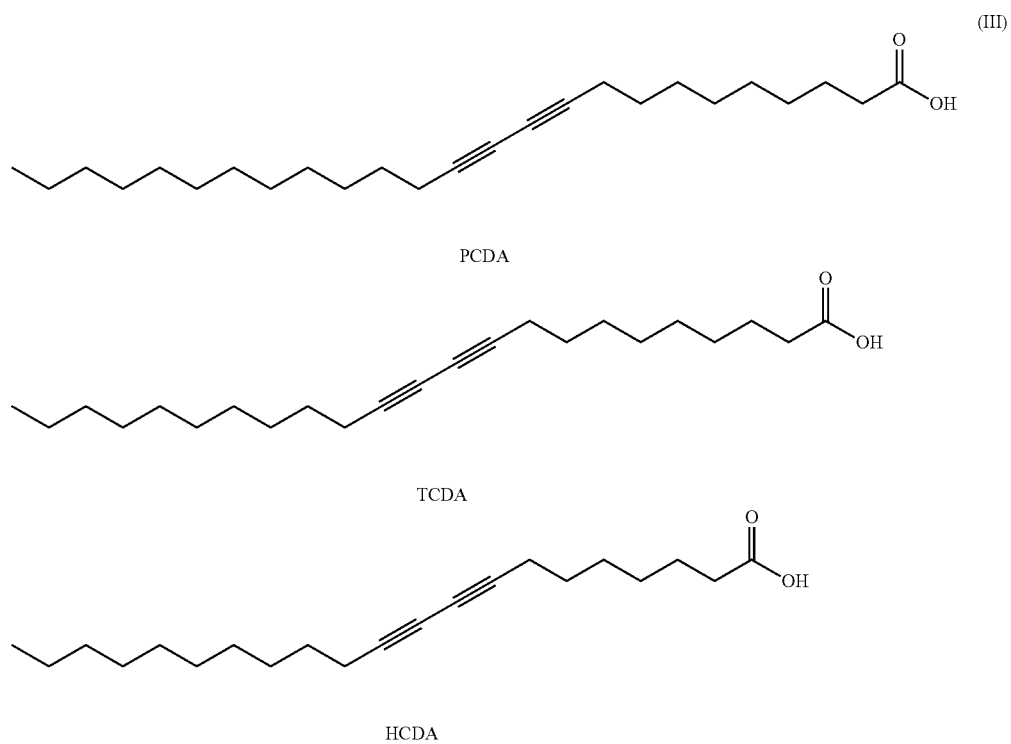

3. Diacetylene Carboxylate

A carboxylate salt according to the current teachings is a potassium, rubidium, or a cesium salt of a carboxylic acid that contains at least two conjugated triple bonds. As described in formulas 1 and 2 above, the carboxylate salt contains a carboxylate group attached to a hydrocarbyl group that contains 10 or more carbon atoms and contains conjugated triple bonds. The hydrocarbyl group of the carboxylate salt is like the group R defined above in Formula (I) and Formula (II).

More specifically, suitable carboxylate salts are salts of diynoic carboxylic acids that contain 18 to 30 carbon atoms. The specific examples include carboxylate salts that contain 20, 21, 22, 23, 24, or 25 carbon atoms. By diynoic acid is 4. Water Soluble Polymer The water-soluble polymer is selected from polymers that do not interfere with the water sensing function and provide the described benefits. Thus, the water-soluble polymer applied to the carboxylate salt coated substrate permits a subsequent photopolymerization of conjugated triple bonds in situ by ultraviolet radiation. In preferred embodiments, the coating of water-soluble polymer protects the hydrochromic film from delaminating or removing itself from the substrate when it is exposed to water in its use as a water sensor.

For example, polyvinyl alcohol has been shown to be suitable. The polyvinyl alcohol is hydrolyzed to such an extent that it becomes water soluble. Examples include 80% hydrolyzed PVA and 100% hydrolyzed PVA. Non-limiting examples include 100% hydrolyzed PVA having a weight average molecular weight from 77,000 to about 79,000, and 80% hydrolyzed PVA having a weight average molecular weight of about 80,000.

5. Coating the Carboxylate Salt and Water Soluble Polymer

The carboxylate salt and the water-soluble polymer are coated on the substrate in sequence, preferably with drying in between. The salt and the polymer can be coated on the paper by any suitable means, such as dip-coating, spin-coating, contact-coating and the like. Alternatively, a solution of the carboxylate salts or the water-soluble polymer is applied by spray coating. The amount of respective component added onto the substrate depends on the concentration of the solution used to apply the component and the time of exposure. For automated processes, a solution can be set to spray at a predefined rate. A substrate is drawn past the spray nozzle at a predetermined speed. The amount of the component thus coated onto the substrate depends on the concentration in the solution being applied, the rate of spray, and the rate of travel of the substrate past the spray equipment.

If the substrate is to be dip-coated by dipping or immersion (partial or complete) into a solution of the salt or polymer, the amount applied depends upon the concentration of the solution, the time of dipping/immersion, the temperature, and other factors. In a non-limiting example, a solution of the carboxylate salt used for coating the substrate contains 0.1 to 20 weight % of the diynoic acid salt and the polymer solution contains 0.1 to 20% of the water soluble polymer. In various embodiments, suitable sensors are manufactured when a substrate is dipped into such solutions for a time on the order of a few seconds such as for 1 second, 2 seconds, 3 seconds, or up to about 10 seconds in non-limiting examples. In general, it is desirable to avoid too long a dipping time, especially when the substrate is paper, paper board, or other material that could potentially swell or fall apart in water. Specific examples of these parameters are given in the working examples that follow.

In preferred embodiments, the coated substrate is dried after application of the carboxylate salt solution and before the coated substrate is exposed to the solution of the water soluble polymer. Drying can be achieved in various embodiments by heating, exposing to vacuum, letting stand under ambient conditions, or any combination of these. Although it is believed that drying after applying the carboxylate salt leads to better adherence of a subsequently coated water soluble polymer, it is acceptable under certain circumstances to dry the coated carboxylate salt partially or not at all before exposing the substrate to a subsequent coating of water soluble polymer.

Figure 2:
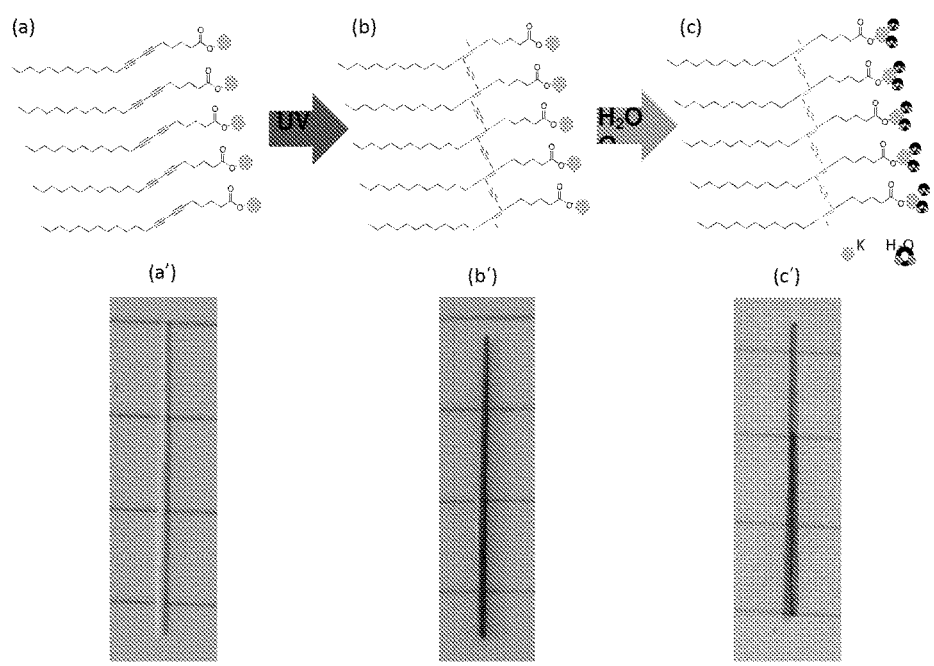
FIG. 2 illustrates various embodiments of diacetylene carboxylic acids for use in one aspect of the invention.

After the water-soluble polymer is applied and the substrate preferably dried, the carboxylate salt can be photopolymerized in situ to form the water sensor. Preferably, the substrate is formed into the final shape and size of the water sensor before the photopolymerization takes place. The process is illustrated in FIG. 2. FIG. 2 shows photographs of a paper tip coated with the carboxylate salt before and after a photopolymerization and exposure to water. In FIGS. 2a and 2a' the coated substrate is illustrated after application of the water-soluble polymer, but before photopolymerization of the conjugated triple bonds of the carboxylate salt. In FIGS. 2b and 2b', the upper cartoon illustrates the conjugated backbone formation achieved by photopolymerization of the triple bonds, while the lower photograph shows the sensor having changed color to blue. Finally, FIGS. 2c and 2c' illustrate in the upper cartoon the structure when the photopolymerized coating is exposed to water. Although the color in FIG. 2c' cannot be seen in the black and white figures, the sensor in FIG. 2c' is red, reflecting its color change upon exposure to water.

Thus, FIG. 2 shows optical images of a paper tip coated with a water-soluble polymer and with a carboxylate salt complex before and after photopolymerization and exposure to water. Successful blue color development in FIG. 2b' shows that the coating of the water-soluble polymer does not prevent or hinder the photopolymerization of the carboxylate salt.

Further, the role of the water-soluble polymer coating layer is to prevent the carboxylate salt from dissolution in the water. When the paper tip is soaked with water, the carboxylate salt complex changed color from blue to red, but was not removed from the paper tip.

Various parameters of the sensor described herein can be varied to achieve sensitivity and response time desired in a particular application. For example, the sensitivity and response time can be affected and controlled by the composition of the carboxylate salt coating, the nature of the water-soluble polymer, the thickness of the individual coating layers. The latter, in turn, is a function of parameters discussed above.

6. Substrate

The substrate can be made of any material suitable for the intended use. In a non-limiting example, if the substrate is paper or paper board and is rolled into a paper tip, as illustrated, for example in FIG. 2. One application of this kind of sensor is to probe tissues to determine if there is water in the tissue. An example of this is using the water sensor after oral surgery to probe whether there is any water left in the wound or surgical incision that needs to be protected from water. In such applications, it is advantageous that the water sensors described herein tend not to change color upon exposure to relative humidity in a gas, such as would be found in the oral cavity of the patient. Rather, the color change is observed only when sensor is applied to a tissue, where it responds to the presence of liquid water.

EXAMPLES

The invention has been described above with respect to various preferred embodiments. Further non-limiting description is given in the working examples that follow.

Example 1

Synthesis of Diacetylene Monomer

All solvents were purchased from Sigma-Aldrich. 10,12-pentacosadiynoic acid (PCDA) was purchased from GFS Chemicals. Oxalyl chloride and alginic acid were obtained from Acros Organics. 5-aminoisophthalic acid, lithium hydroxide, sodium hydroxide, potassium hydroxide and calcium chloride were purchased from Sigma-Aldrich.

To a solution containing 1.00 g (2.67 mmol) of PCDA in 20 mL of methylene chloride was added dropwise 0.81 g (8.01 mmol) of oxalyl chloride and a catalytic amount of DMF at room temperature. The resulting solution was stirred at room temperature for 2 hours, concentrated in vacuum, giving a residue which was re-dissolved in 10 mL of methylene chloride. The resulting solution was added dropwise to a solution containing 0.58 g (3.20 mmol) of 5-aminoisophthalic acid in 15 mL of pyridine. The resulting mixture was stirred for 12 h at room temperature and poured into cold water to yield a precipitate containing the desired diacetylene monomer PCDA-IPA as an off-white solid. NMR spectrum of the solid was consistent with the structure shown above.

Example 2

Preparation of Nanofiber Suspension

PCDA-IPA (80.65 mg) is cotton-filtered to make unpolymerized white powder added to a 15 ml of 20 mM LiOH (NaOH or KOH) solution. The mixture solution was heated to 90° C. with stirring until the PCDA-IPA is completely dissolved in LiOH (NaOH or KOH) solution, and the final resulting solution appears to be transparent. The resulting solution was stored in refrigerator for overnight.

Example 3

Preparation of PDA Fiber Embedded Alginate Hydrogel 10 mM PCDA-IPA/Li fiber nanofiber suspension of Example 2 was homogeneously mixed with 4% alginic acid solution in a 20 ml vial. To the solution, 2% calcium chloride solution is added to generate crosslink gel, than stirring was continued at room temperature for 30 min to crosslink fully. After stirring, the hydrogel is washed with DI water for 3 times. The hydrogel is placed on a substrate, and is dried at 40° C. for 2 hours in an incubator. Then, the dried hydrogel is photo-polymerized under 254 nm UV light until the blue color develops.

Example 4

Photographs of photopolymerized alginate hydrogels embedded with various monomer structures have a blue color before exposure to water. When a monomer like the PCDA-IPA of Example 1 is exposed to a solution of sodium ions, a microcrystal is formed. Exposing the monomer to potassium ion forms a nanofiber of having a diameter of approximately 50 nanometer. Exposing the monomer to lithium ion, on the other hand, forms a nanofiber having a diameter of 20 nanometer. The photographs of the various hydrogels having the microcrystal, potassium nanofiber, or lithium nanofiber, show that only the last one, (the lithium PCDA-IPA) shows a colorimetric response, in that the hydrogel turns red upon exposure to water. The color change is illustrated in FIG. 1 which shows the absorbents of the dried gel before exposure to water and the frozen gel after exposure to water. At a red wavelength around 675 nanometers, the absorbance of dried hydrogel is greater than that of the swollen hydrogel. This means, as absorbance at the red wavelength goes down, the hydrogel takes on a more reddish color when it swells upon exposure to water. Similarly, FIG. 1 shows that absorbance at a blue wavelength of about 525 nanometers, to give an example, increases when going from the dried to the swollen (wet) state. Thus, as absorbance of the blue wavelength increases, the appearance of hydrogel likewise tends to look redder.

It is to be noted that nanofibers having approximate of 50 nanometers can be formed from the interaction with potassium ions and the monomer like PCDA-IPA of Example 1. However, photomicrographs of photopolymerized alginate hydrogel made from the potassium nanofibers shows no visible color change upon exposure to moisture. To illustrate, the nanofiber made from potassium ions and PCDA-IPA is characterized by a colorimetric response of about 2-2.5, while colorimetric response of our corresponding nanofiber made from lithium ion and PCDA-IPA is on the order of 16 or 17. For determining the colorimetric response (CR), the blue percentage (PB) is defined as $PB=A_{blue}/(A_{blue}+A_{red})\times 100\%$ where $A_{blue}$ is the absorbance at the peak around 675 nm and Ared is the absorbance at the peak around 525 nm. Then, the CR is defined as CR=(initial PB−final PB)/initial PB×100%.

Example 5

Sensor Made with Potassium Salt of a Diynoic Acid and Polyvinyl Alcohol 6,8-heneicosadiynoic acid (HCDA), a diacetylene monomer, was reacted to make the potassium salt. 48 mg of HCDA and 18 mg of KOH (potassium hydroxide) were dissolved in THF (0.4 ml) and water (0.05 ml), respectively. 0.05 ml of the KOH aqueous solution was added dropwise into the HCDA/THF solution. Next, 0.05 ml of methanol was added and the resulting mixture was stirred at an ambient temperature for 1 h. The final concentration of HCDA in the solution and the ratio of HCDA and KOH is 3 mM and 1:5, respectively (about 11 wt %, 66 mg/0.5 ml). The solution was coated onto a paper tip via dip coating (for 5 seconds), after which the coated paper is dried in vacuum for 10 min. After complete drying, the HCDA-coated paper tip is dipped in a 2.5 wt % solution of polyvinyl alcohol (80% hydrolyzed, $M_w$ about 80,000) to make a thin PVA layer. UV Irradiation (254 nm) on the resulting film for few seconds produced a blue color, confirming successful photopolymerization of the coated composition. Performance is illustrated in FIG. 2.

What is claimed is:

1. A method of making a sensor that changes color on exposure to moisture, comprising:
    coating a solution of a carboxylate salt on a substrate;
    drying the coated substrate;
    exposing the dried substrate to a solution of water-soluble polyvinyl alcohol; and
    irradiating the coated substrate with ultraviolet radiation;
    wherein the carboxylate salt is a potassium, rubidium, or cesium salt of a carboxylic acid comprising a carboxylate head and an aliphatic tail, and
    wherein the aliphatic tail comprises two conjugated triple bonds.

2. The method of claim 1, wherein the salt is a potassium salt.

3. The method of claim 1, wherein the carboxylic acid has 16-30 carbon atoms.

4. The method of claim 3, wherein carboxylic acid has 18-28 carbon atoms.

5. A water sensor that changes color from blue in the dry state to red in the presence of water, comprising:
    a substrate;
    a polymerized diacetylene carboxylate salt coated on the substrate; and
    a water-soluble polymer disposed on the substrate over the polymerized diacetylene carboxylate salt;
    wherein the carboxylate salt is a potassium, rubidium, or cesium salt of a carboxylic acid comprising a carboxylate head and an aliphatic tail, and
    wherein the aliphatic tail comprises two conjugated triple bonds.

6. The water sensor according to claim 5, wherein the water-soluble polymer comprises polyvinyl alcohol.

7. The water sensor according to claim 5, wherein the carboxylate salt is a potassium salt.

* * * * *